(12) United States Patent
Mäntylä et al.

(10) Patent No.: US 7,834,161 B2
(45) Date of Patent: *Nov. 16, 2010

(54) PROCESS FOR PROTEOLYTIC CLEAVAGE AND PURIFICATION OF RECOMBINANT PROTEINS PRODUCED IN PLANTS

(75) Inventors: Einar Mäntylä, Reykjavík (IS); Björn Lárus Örvar, Kopavogur (IS)

(73) Assignee: ORF Liftaekni hf., Reykjavik (IS)

( * ) Notice: Subject to any disclaimer, the term of this patent is extended or adjusted under 35 U.S.C. 154(b) by 988 days.

This patent is subject to a terminal disclaimer.

(21) Appl. No.: 10/569,677

(22) PCT Filed: Aug. 27, 2004

(86) PCT No.: PCT/IS2004/000011

§ 371 (c)(1),
(2), (4) Date: Aug. 21, 2006

(87) PCT Pub. No.: WO2005/021764

PCT Pub. Date: Mar. 10, 2005

(65) Prior Publication Data

US 2007/0107085 A1    May 10, 2007

Related U.S. Application Data

(60) Provisional application No. 60/497,935, filed on Aug. 27, 2003.

(30) Foreign Application Priority Data

Aug. 27, 2003   (IS) .......................................... 6929

(51) Int. Cl.
*A23J 1/00* (2006.01)
*C12N 15/09* (2006.01)
*C12N 15/82* (2006.01)
*C12P 21/06* (2006.01)

(52) U.S. Cl. .................. 530/412; 435/69.7; 435/69.1; 800/278; 530/413

(58) Field of Classification Search ................. 530/412, 530/413; 435/69.7, 69.1; 800/278
See application file for complete search history.

(56) References Cited

U.S. PATENT DOCUMENTS

6,048,715 A      4/2000   Haynes et al.
7,462,701 B2 *  12/2008  Mantyla et al. ............. 530/412
2002/0164718 A1  11/2002  Tchaga et al.

FOREIGN PATENT DOCUMENTS

WO   WO-00/77174 A   12/2000
WO   WO-02/05922 A   1/2002

OTHER PUBLICATIONS

Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of a b-ketoacyl synthase to a malonyl decarboxylase by replacement of the active-site cysteine with glutamine. Biochemistry, 1999, vol. 38: 11643-11650.*
Boraston, Alisdair B et al., Protein Expression and Purification, vol. 21, No. 3, Apr. 2001, pp. 417-423.
Boraston, Alisdair B et al., Biochemistry, vol. 40, No. 21, May 29, 2001, pp. 6240-6247.
Reeves, R.A. et al., Applied and Environmental Microbiology, Apr. 2000, vol. 66, No. 4, pp. 1532-1537.
Chhabra, S.R. et al., FEBS Letters, Elsevier Science Publishers, vol. 531, No. 2, Nov. 6, 2002, pp. 375-380.

* cited by examiner

*Primary Examiner*—Ganapathirama Raghu
(74) *Attorney, Agent, or Firm*—Birch, Stewart, Kolasch & Birch, LLP

(57) ABSTRACT

The present invention relates to improved methods for protein purification of high-value heterologous proteins by providing fusion proteins suitable for affinity purification and improved and economical methods of proteolytic cleavage of fusion proteins. The methods are useful for large-scale production of purified recombinant proteins from plants, plant-derived tissue or plant cells. The invention aims to reduce the cost and improve the quality of downstream processing of heterologous proteins produced in plants and other biological production systems.

21 Claims, 3 Drawing Sheets

SEQUENCE LISTING

<160> NUMBER OF SEQ ID NOS: 2

<210> SEQ ID NO 1
<211> LENGTH: 564
<212> TYPE: DNA
<213> ORGANISM: Thermotoga maritima

```
<400> SEQUENCE: 1
gtggccaccg ccaagtacgg caccccagtg atcgacgggg agatcgacga gatctggaac      60
accaccgagg agatcgagac caaggccgtg gccgtgggga gcctcgacaa gaacgccacc     120
gccaaggtgc gcgtgctctg ggacgagaac tacctctacg tgctcgccat cgtgaaggac     180
ccagtgctca acaaggacaa cagcaacccc tgggagcaag acagcgtgga gatcttcatc     240
gacgagaaca accacaagac cggctactac gaggacgacg acgcccaatt ccgcgtgaac     300
tacatgaacg agcaaaacct tcgggaccgg gggagcccag cccgcttcaa gaccgccgtg     360
aagctcatcg aggggggcta catcgtggag gccgccatca agtggaagac catcaagcca     420
accccaaaca ccgtgatcgg cttcaacatc caagtgaacg acgccaacga gaaggggcaa     480
cgcgtgggga tcatcagctg gagcgaccca accaacaaca gctggcgcga cccaagcaag     540
ttcgggaacc tccgcctcat caag                                            564

<210> SEQ ID NO 2
<211> LENGTH: 705
<212> TYPE: DNA
<213> ORGANISM: Homo sapiens

<400> SEQUENCE: 2
atcgtcggcg ggagcgattc cagggagggc gcatggccat gggtcgtggc actctacttc      60
gatgatcaac aagtctgcgg ggcatccctg gtgagcaggg attggctcgt gtccgcagca     120
cattgcgtgt acggcaggaa catggagcca tccaagtgga aggcagtgct cggcctgcat     180
atggcatcca acctcacctc cccacaaata gagaccaggt tgatcgatca aatcgtcata     240
aacccacatt acaacaagcg gaggaagaac aacgacatcg caatgatgca tctcgagatg     300
aaggtgaact acaccgatta catacaacca atctgcttgc cagaggagaa ccaagtgttc     360
ccaccaggga ggatctgctc catcgcaggc tggggcgcac tcatatacca agggtccacc     420
gcagatgtac tgcaagaggc agacgtgcca ctcctctcca acgagaagtg ccaacaacaa     480
atgccagagt acaacatcac cgagaacatg gtgtgcgcag gctacgaggc aggcggggta     540
gattcctgcc aaggcgattc cggcgggcca ctcatgtgcc aagagaacaa caggtggctc     600
ctggcaggcg tgacctcctt cggctaccaa tgcgcactcc caaaccggcc aggggtgtac     660
gcacgggtgc caaggttcac cgagtggata caaagcttcc tccat                     705
```

PROCESS FOR PROTEOLYTIC CLEAVAGE AND PURIFICATION OF RECOMBINANT PROTEINS PRODUCED IN PLANTS

FIELD OF THE INVENTION

The present invention is in the area of biochemistry and protein technology and relates to improved methods of isolation and purification of heterologous proteins especially from transgenic plant material. Furthermore, the present invention presents an improved and economical way of proteolytic cleavage of fusion proteins.

BACKGROUND

Protein based biopharmaceuticals show great promise in providing more specific and tissue specific, or cell specific drug treatments against serious diseases (for overview see "Recombinant Protein Drugs" Ed. P. Buckel 2001).

Numerous examples in the prior art have demonstrated the use of microorganisms such as bacteria, and animal cells for the production of such biopharmaceuticals; of which insulin is a notable example.

Many examples in the literature have demonstrated the utilization of transgenic plants or plant cell cultures for expression and manufacturing of high-value heterologous polypeptides or biopharmaceuticals. Such plant-based manufacturing process may be called molecular farming.

Production of valuable proteins can be made more economical by the use of plants as production organisms. The cultivation cost for plants used as host organisms for protein manufacturing can be considerably lower compared to most production systems based on bioreactors, such as prokaryotic production systems, animal cell cultivation and so forth. However, for all of the above production systems, purification of heterologous proteins remains a demanding and a costly task. Thus, for plant-based production systems, downstream processing generates most of the production costs in the manufacturing of high-value heterologous proteins.

Protein purification and isolation is a key process in downstream processing of proteins accumulated and produced in a variety of host organisms by the use of gene technology. The purification of proteins from the host organisms can be quite laborious, complex and expensive. A variety of chromatographic strategies are used commercially for separation and purification of proteins of interest from production host organisms. The chromatographic strategies may rely on physicochemical differences between contaminating or endogenous proteins and the heterologous protein of interest, such as in size, solubility, charge, hydrophobicity, and affinity.

Combinations of chromatographic strategies consisting of multiple steps, require several expensive chromatography matrices and the necessary hardware consisting of columns, control units and so forth, and are accompanied by product yield-losses at each step, and consequently, economical losses. In addition to the chromatographic steps involved, downstream processing typically involves multiple filtering and centrifugation steps. As a result, the cost of purification and downstream processing may become prohibitive for the purification of a protein based biotechnological product. As for a number of protein-based products of lesser value, such as industrial proteins, the cost of downstream processing can be inhibitory for their use and marketing, resulting in crude and poorly defined products. For most biotechnology products purification costs are certainly a major proportion of the manufacturing costs.

The cost of specialized chromatography matrices effecting the separation of a protein of interest from contaminants is high as a result of complex coupling chemistry involved in their production. The chemical complexity of these matrices may cause unwanted leaching of ligands and other substances from the matrix during a purification procedure, where necessary preventive measures, monitoring, or the removal of leachates from the protein of interest add to the already high cost of downstream processing.

Affinity chromatography is among the most powerful purification principles as it is based on specific affinity between an agent and a specific ligand, often mimicking a natural protein-ligand interaction. Several different kinds of affinity adsorbents are available, some highly specific for a particular protein, others binding to classes of proteins rather than particular proteins.

In many cases affinity chromatography relies on the presence of a specific tag attached to the heterologous protein of interest through recombinant gene technology. This tag needs to be cleaved off when it has served its purpose during purification of the heterologous product of interest. This cleavage is achieved with the use of a highly specific protease that cuts the amino acid backbone of the protein at a specific cleavage site, that was introduced between the tag and the protein of interest during cloning stage. The necessity to efficiently separate the protease and the resulting cleavage products from each other adds to the complexity, number of purification steps involved and the cost of processes utilizing such site-specific proteolytic cleavage. The cost involved in the use of such a specific protease is often inhibitory to the industrial use of tag-based affinity chromatography, and therefore limiting the use of this powerful purification technique. Ways of more economic and efficient use of specific proteases could be enabling for the bioprocessing industry and possibly lower the cost of production of purified recombinant proteins in general.

In many cases affinity chromatography implies the use of an immobilized ligand to an adsorbent that specifically selects out proteins binding to that ligand. The coupling of ligands to affinity adsorbents involves the use of coupling chemistry such as cyanogen bromide-, tosyl-, or vinylsulfone-activation of adsorbents. The ligand coupled to the column matrix may or may not be of proteinaceous origin. Examples of the former are, but not limited to, immobilized protein A or protein G having affinity for γ(gamma)-globulin, therefore being useful in the purification of antibodies, and lectins with affinity for glycoproteins. As an example of the latter, immobilized glutathione coupled to matrix binds fusion proteins containing a glutathione S-transferase domain. Immobilized metal affinity chromatography (IMAC) is based on immobilization of metal-chelating ligands to a matrix and relies on the formation of weak coordinate bonds between metal ions immobilized on a column and basic groups on proteins, mainly histidine residues.

Commercial cloning vectors provide for cloning of a cDNA in frame with a string of histidine residues—a His-tag, that enables the purification of the resultant fusion protein with IMAC. Although widely used for small-scale purification of proteins, IMAC is a non-specific but selective method, as native histidine residues in contaminating proteins can lead to binding in IMAC (Scopes 1993). Several different kinds of tags or binding domains are available in commercial expression vectors resulting in fusion proteins where the tag/binding domain binds the fusion protein to a ligand coupled onto a column matrix.

High specificity of protein binding can be achieved with these matrix-ligand systems. In the cases mentioned above, complex coupling chemistry is involved to immobilize a ligand onto an inert matrix. Consequently, the cost of an affinity matrix can be often become inhibitory to industrial scale applications of this powerful technique.

Furthermore, as with most other types of chromatography methods, the stability of the coupling of the ligand to the matrix becomes an issue and leaching is of great concern. Heavy metal leaching in IMAC can cause unacceptable and serious contamination in many sensitive purification processes for bioactive proteins, and may inactivate proteins being purified (Scopes 1993).

It is not uncommon that the binding affinity of a protein to its ligand is so strong that conditions for elution, to disrupt the ligand-protein binding, require drastic conditions that partly denature the valuable protein being purified. A non-limiting example of this is the elution of antibodies from Protein A-affinity matrix, requiring denaturing at low pH to release the antibody from the column. Including a denaturing step in a protein purification process is undesirable due to the risk of loss of activity of the purified protein, the addition of an extra step for refolding the protein and subsequent activity analysis requirements for the refolded protein product, and the added cost involved.

To enable the use of affinity-based chromatography for large scale purification from plants, it is highly desirable to develop a purification process that is simpler and more economic than the current measures commercially available, with less coupling chemistry involved and compatible with the quality requirements of the pharmaceutical industry standards.

Polysaccharides and polysaccharide binding proteins may be used in conjunction for the design of an affinity chromatography step (see, e.g., Boraston et al., 2001).

U.S. Pat. No. 6,331,416 by Shani et al. describes a method of expressing a recombinant protein with a polysaccharide binding domain that binds to the cellulose in the host plant cell walls, and a protein purification process utilizing the affinity of this protein to poorly defined host plant cellulose, resulting in a cell wall-protein complex that can be separated from soluble contaminating proteins. The strength of binding can be such that releasing the protein from the cellulosic host plant matter may require drastic conditions that denature the protein, having negative effects on the activity of the recombinant proteins being purified. The complications involved are comparable to those mentioned above for antibody-Protein A elution.

The carbohydrate binding domain CBM9-2 is from the *Thermotoga maritima* Xylanase 10A (Winterhalter et al 1995: Mol. Microbiol. 15 (3), 431-444). The CBM9-2 genomic DNA sequence is available as GenBank Accession No. Z46264 and it belongs to the Family IX of CBM-s and has number of attractive properties for high-resolution affinity purification, including non-denaturing eluting conditions using 1M glucose as a eluent, and high specific affinity for amorphous as well as crystalline celluloses (Boraston et al. 2001: Biochemistry 40, 6240-6247).

Plant-based production of proteins shows great promise for large scale manufacturing of proteins in an economic manner, as has been shown by examples in literature (for overview see Hammond 1999).

The cultivation costs involved in molecular farming with plants are considerably lower than with traditional bioreactor-based methods.

There is a recognized need for a downstream process for purification of heterologous proteins from transgenic plant material that is efficient, simple, and economical. Furthermore, there is a need for such a downstream process consisting of gentle, non-denaturing conditions for the protein of interest, (in particular, specific affinity purification methods with gentle elution conditions) in order to secure bioactivity of the protein of interest, and improve yields.

A protein purification process free from the limitations detailed above could significantly lower the production cost involved in the production of biopharmaceuticals from plants, and would be enabling for the purification of heterologous proteins of value for which downstream processing has been prohibitively complex and costly.

SUMMARY AND OBJECTS OF THE INVENTION

The primary objective of present invention is to provide an improved method for protein purification of high-value heterologous proteins produced in plants, plant derived tissue or plant cells, and means for efficient and economical proteolytic separation of heterologous protein of interest from a fused affinity tag such as e.g. a CBM fused to the protein.

The invention aims to reduce the cost and improve the quality of downstream processing of heterologous proteins produced in plants.

An important feature of the purification process is the inherent separation of the protein of interest as a CBM-fusion protein from cell-wall fragments and other poorly defined plant-derived solids as CBM-fusion proteins of the invention do not bind to these components. This can be done separately prior to an affinity chromatography step or simultaneously with an affinity chromatography step.

In a first aspect, the invention provides a method for production and purification of a soluble heterologous fusion protein comprising a cellulose binding module (CBM), from transgenic plants or transgenic plant cells expressing said fusion protein, the method comprising:

disrupting the transgenic plant material;

adding an extraction liquid to the plant material, thereby creating a mixture of soluble and insoluble plant material, so as to extract the soluble fusion protein from said disrupted plant material to the liquid phase to obtain a protein extract;

separating the insoluble plant material, comprising cell-wall material and solids, from said protein extract comprising said fusion protein of interest;

contacting said protein extract, to a polysaccharide matrix which binds to said fusion protein;

washing the matrix with the bound fusion protein with one or more suitable aqueous solutions such as one or more buffer solutions, i.e., the washing may be preformed in one step, with a gradient or as a sequence of different washing solutions; and eluting the fusion protein from said polysaccharide matrix by adjusting conditions effecting the release of said fusion protein from the matrix.

Typically, the transgenic plant or plant cell is selected from the group of dicotyledonous plants and monocotyledonous plants, and in preferred embodiments said plant cell or transgenic plant is from the group of tobacco, rape seed, soy bean, alfalfa, lettuce, barley, maize, wheat, oat and rice.

The separation step comprises in some embodiments a method selected from expanded bed adsorption (EBA), packed mode chromatography, precipitation, filtration, centrifugation, or any combination thereof.

The affinity binding step binding the fusion protein to a polysaccharide matrix preferably comprises a chromatography step.

However, in certain useful embodiments, said separation of cell-wall fragments and other poorly defined plant-derived solids from the protein of interest—the CBM-fusion protein, and the affinity binding of the CBM fusion protein to a polysaccharide matrix can be done in a single powerful purification step using Expanded Bed Adsorption chromatography (EBA) with a suitable, inexpensive polysaccharide matrix. This feature streamlines and improves the economy of the downstream processing.

In advantageous embodiments of the present invention, the polysaccharide matrix comprises cellulose, and preferably pharmaceutically compatible cellulose. Such a well-defined pharmaceutical grade cellulosic matrix to which the CBM-fusion protein binds allows various high-end uses of the purified heterologous protein. A useful pharmaceutically compatible cellulose material for use as the polysaccharide matrix comprises Avicel™ (FMC Corporation, PA, USA).

The polysaccharide matrix used for affinity chromatography according to the invention requires no complex coupling chemistry or immobilization of potentially leaching ligands. The polysaccharide matrix provides both structural support and rigidity while constituting the affinity adsorbent itself. Thereby, more economical and safer protein purification is enabled for plant derived heterologous proteins.

It is still an advantage of this invention that the process described is amenable for different polysaccharide matrices of differing qualities all according to the different end-use of the purified heterologous proteins e.g. in for example agriculture, chemical industry or pharmaceutical industry. An affinity adsorbent made out of polysaccharide of pharmaceutical grade is a bulk material within the pharmaceutical industry and is considerably less expensive than any commercially available affinity chromatography media. Thus, an affinity matrix of very high quality can be made economical using the process described by this invention, enabling more economical downstream processing of high-value proteins from plant derived material.

It is a further advantage of the present invention that once the plant derived CBM-fusion protein is bound to the polysaccharide chromatography matrix, and after washing the matrix to remove any contaminating endogenous plant proteins, the fusion protein can be eluted from the column using non-denaturing, mild conditions typically neutral or acidic conditions and preferably with the addition of soluble carbohydrates (sugars), that preserve the activity and structure of any fusion partner protein attached to CBM. The sugars compete with cellulose for the binding sites of CBM and a suitable concentration will release substantially all of the bound CBM fusion protein.

It follows that the preferred CBM-s that are used in the methods of the invention and fused to the heterologous protein of interest are such CBM-s that have desired binding characteristics to allow sufficiently strong binding to a suitable polysaccharide matrix to obtain a high yield of bound CBM fusion protein, and releasing by such mild conditions as described above. CBM9-2 has been found to have these desired characteristics. The use of other CBM-s with such characteristics is also within the scope of the invention. Such CBM-s may be found e.g. by searching available gene databases for sequences encoding CBM having desired characteristics, e.g. sequence motifs found to be similar to motifs in CBM9-2 that are important for the binding characteristics. Also, existing CBM-s may be modified with point mutation techniques well known in the art to modify their binding characteristics in order to obtain suitable CBM-s according to the invention.

After the fusion protein has been eluted from the polysaccharide affinity matrix it may optionally be subjected to one or more further purification or isolation steps, depending on the desired form and use of the protein.

In useful embodiments, the transgenic plant or plant cell comprises a nucleic acid sequence encoding for a CBM, preferably the CBM is heat-stable and remains soluble at elevated temperatures. The term heat-stable in this context indicates that the protein remains soluble, correctly folded and active at elevated temperatures, i.e. temperatures above about 25° C., and typically above about 37° C., including the range of 40° C.-100° C.

Genes encoding such preferred CBM may be obtained from thermophilic organisms, including thermophilic bacteria, algae and fungus and introduced into the host plant or plant cell in such a way as to express a fusion protein comprising said CBM. The term thermophilic refers herein to organisms with optimal growth temperature over 40° C. A preferred CBM is coded for by the xylanase10A gene from *Thermotoga maritima*, preferably the region within the host plant or plant cell that codes for a CBM is a region of said gene. Said region coding for a CBM may in certain embodiments comprise a sequence depicted as SEQ ID NO: 1, or a nucleic acid sequence encoding the same amino acid sequence, or a sequence encoding an amino acid sequence with substantial sequence identity to said amino acid sequence.

It may be useful in some embodiments of the invention to heat the protein extract comprising the soluble fusion protein, such as to a temperature in the range of 37° C. and 100° C., e.g. a temperature in the range of 50-80° C., for a period of time such as in the range of from 1 min to 120 minutes during the process. For this purpose, heat-stable CBM such as from thermophilic sources is particularly useful. During such heating, a part of the endogenous plant proteins may become inactivated and/or denatured and may thus readily be separated from the protein extract. Said heated extract may preferably be subjected to the process step comprising expanded bed adsorption with a polysaccharide matrix for the simultaneous separation of solids and affinity binding of said CBM fusion protein from the heated extract.

In particular embodiments of the invention, said heterologous fusion protein comprises a protease (indicating a proteolytically active polypeptide), which in certain useful embodiments is a mammalian enterokinase (EK) or an enterokinase-active part thereof, e.g., a bovine EK or a bovine EK catalytic domain (EKc). A useful EKc for this purpose is encoded for by the by the nucleic acid sequence shown as SEQ ID NO: 2.

In a highly useful embodiment of the invention, said fusion protein comprises a CBM and a heterologous polypeptide of interest intercepted by a stretch of amino acids comprising a proteolytic cleavage site, preferably a proteolytic cleavage site recognized and cleaved by a specific protease. By having such a site, the CBM can readily be cleaved off the fusion partner in the fusion protein to obtain the desired heterologous protein without the accompanying CBM.

Hence, in a related aspect, the invention provides a process for purification of a heterologous protein of interest, the process comprising
  (a) providing a fusion protein comprising said heterologous protein fused to a CBM as defined herein above, intercepted by a proteolytic cleavage site,
  (b) contacting said fusion protein with a functional protease fused to a CBM at conditions facilitating proteolytic cleavage by said protease, to cleave the fused CBM from the heterologous protein of interest, (c) contacting the solution of CBM-protease, free CBM and heterologous protein of interest to a polysaccharide matrix, such as defined herein, under conditions where the CBM-protease and free CBM binds to said polysaccharide matrix and where the heterologous protein of interest is not retained on said polysaccharide matrix, (d) separating the non-bound heterologous protein of interest from the polysaccharide matrix, (e) washing the polysaccharide matrix with the bound CBM-protease and CBM, with one or more suitable aqueous solutions, (f) eluting the CBM-protease from the matrix by adjusting conditions effecting the release of said CBM-protease off the matrix; and (g) optionally reconditioning said eluted CBM-protease, to retain its affinity to said polysaccharide matrix, such that the reconditioned CBM-protease can be re-used for subsequent repetition of the process.

The steps of binding the fusion protein, washing and eluting are preferably conducted such as described above.

In preferred embodiments, the protease fused to CBM is enterokinase, preferably as described above. Such a CBM-fusion protease, EK or other type, may suitably be produced and purified by the methods described herein.

It will be appreciated that the method described above may advantageously be combined with the above method to produce and purify a soluble heterologous fusion protein, such as to obtain a desired heterologous protein expressed and isolated initially as a CBM fusion protein, in a purified form free from the fused CBM.

An additional advantage of the method is the possibility of recycling the protease used, i.e. using the same protease repeatedly for batch production of the desired protein expressed as a CBM fusion protein, which makes the processes described herein even more economical. This is readily accomplished as the CBM-fused protease is designed without having a proteolytic cleavage site, so as to hinder cleavage of the CBM from the CBM protease itself. Furthermore such recycling is made possible by the mild conditions used for elution, as described by hereinabove, thus not compromising the activity of the eluted protease.

Thus, it is a further advantage of the invention that it provides a process enabling recycling of costly, specific proteolytic enzymes, thus additionally improving the economy of affinity purification in downstream processing of heterologous proteins, such as in particular, but not limited to proteins obtained from genetically modified plants, plant derived material and plant cells.

The present invention successfully addresses the shortcomings of downstream processing involved in of heterologous protein production at large scale, for purposes such as, but not limited to, agriculture, chemical industry and the production of protein-based pharmaceuticals. In particular, it provides a novel process of separating CBM-fusion proteins from biomass such as plant-derived cellulosic material, with fewer processing steps involved, taking advantage of a safer and more economical affinity chromatography principle amenable for use within the pharmaceutical industry, gentle elution conditions maintaining the activity of high-value heterologous proteins, and comprising a process step enabling the recycling of a specific high-value protease in the process.

DETAILED DESCRIPTION OF PRESENT INVENTION

Figure 1:
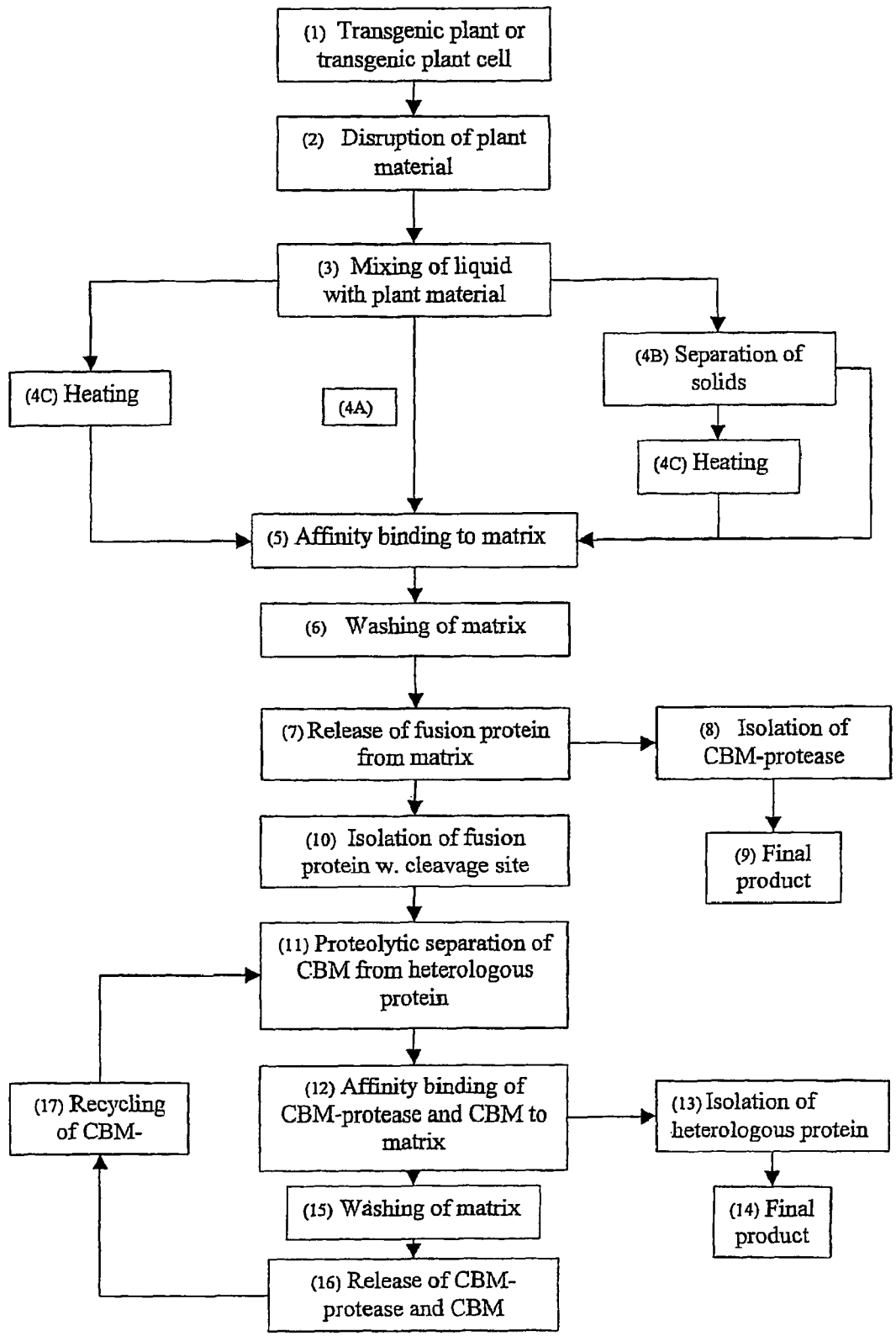
FIG. 1 is a schematic diagram of a preferred embodiment of the process of purification of CBM-protease and the proteolytic cleavage of CBM fusion proteins.

Herein below, the present invention will be described in more detail.

Unless defined otherwise, all technical and scientific terms used herein have the same meaning as is commonly understood and used by one of skill in the art to which this invention belongs.

The term "polypeptide" used herein refers to any polymer of amino acids, being monomeric or multimeric, and does not refer to a specific length of a polymer of amino acids. Thus, for example, the terms peptide, oligopeptide, protein, and enzyme are included within the definition of polypeptide. This term also includes polypeptides with post-expression modifications such as for example, glycosylations, acetylations, phosphorylations and the like.

The term "heterologous polypeptide of interest" or "polypeptide of interest" used herein refers to any polypeptide intended for expression in plant-cells or plant tissue using the methods or compositions of the present invention. As non-limiting examples, pharmacological polypeptides (e.g., for medical uses) or industrial polypeptides (e.g. enzymes) can be produced according to the present invention.

The term "downstream processing" refers to the isolation and purification of a biotechnological product to a form suitable for its intended use.

The term "fusion partner" refers herein to a heterologous protein linked to CBM.

The term "CBM fusion protein" refers to a molecule consisting of a CBM linked to a heterologous protein, and in the context it is put forward in this invention, a molecule without a proteolytic cleavage site, unless described otherwise.

The term "operably linked" refers to a functional linkage between a promoter (nucleic acid expression control sequence, or array of transcription factor binding sites) and a second nucleic acid sequence, wherein the promoter directs transcription of the nucleic acid corresponding to the second sequence.

The term "denatured" refers to a condition of a protein where the native structure, and consequently the activity of the protein is disrupted, and the protein is unfolded or incorrectly folded changing its native three-dimensional structure.

The term "expression" and "production" refer to the biosynthesis of a gene product, including the transcription and translation of said gene product.

"Molecular farming" refers to the operation of using plants of any kind in open fields or in closed facility to express and produce heterologous proteins in their tissue The term "transgenic" refers to any cell, cell line, tissue plant part, organ or organism into which a non-native nucleic acid sequence has been introduced, and therefore altering its genotype, and its progeny thereof in which the non-native nucleic acid is present. Typically, the non-native nucleic acid sequence was introduced into the genotype by a process of genetic engineering, or was introduced into the genotype of a parent cell or plant by such a process and is subsequently transferred to later generations by sexual crosses or asexual propagation.

Transient expression refers to expression in an organisms by genes introduced transiently, without being incorporated in the organism's genome. Thus, transient expression is often limited in time, and the transient genes are not passed to next generations.

"Substantial sequence identity" indicates in the context herein at least 50% sequence identity and more preferably at least 60% such at least 70 sequence identity, such as at least 80% and preferably at least 90% sequence identity, such as at least 95% or 99% sequence identity. Algorithms for sequence analysis are known in the art, such as BLAST, described in Altschul et al., *J. Mol. Biol.* (1990) 215:403-10. Generally, the default settings with respect to, e.g. "scoring matrix" and "gap penalty" will be used for alignment.

The term "transformation" or "transformed" refers to the introduction of a nucleic acid sequence into the DNA genome of a host organism, irrespective of the techniques used for the introduction of the nucleic acid fragment into the host cell.

"Thermophilic" refers to an organism with optimal growth temperature over 45° C.

The term "GMP" (good manufacturing practice) dictates the manner in which biopharmaceuticals and other drugs and medical devices are produced. GMP requirements include standard operating procedures, sterile conditions, validation of materials and equipment and trained personnel.

Monocotyledonous and dicotyledonous plants that can be genetically manipulated can be used in the present invention. Preferably the plant is a monocotyledonous, more preferably barley, and most preferably the barley *Hordeum vulgaris*. A plant that can be genetically transformed is a plant into which non-native DNA sequence, including DNA sequence for a coding region, can be introduced, expressed, stably maintained, and transmitted to subsequent generations of progeny. Genetic manipulation and transformation methods have been used to produce barley plants that are using herbicides including, for instance, bialaphos or basta, or antibiotic, such as hygromycin, as selectable markers.

Methods

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Although only preferred embodiments of the invention are specifically illustrated, numerous modifications and variations in the invention as described in the above examples are expected to occur to those skilled in the art, without departing from the spirit and intended scope of the invention.

Referring to FIG. 1 illustrating a schematic diagram of the purification process for CBM-protease, or for that matter, any CBM-fusion protein, the process can be described as follows:

(1) The starting material for the process is a transgenic plant, material derived from transgenic plants or transgenic plant cells, including, but not limited to, suspension cultures of plant cells as well as undifferentiated cells of calluses. In a variant of the embodiments of the invention the material may be of plant tissue origin expressing transiently a heterologous protein. The material is transgenic in a way that it expresses in a controlled manner a heterologous gene(s) operably linked to a CBM open reading frame, that have been introduced to the plant cells through processes known to a person skilled in the art, such as, but not limited to, *Agrobacterium*-mediated transformation or particle bombardment-mediated transformation or plant viral vector-mediated transformation. The starting material is preferably selected on the basis of satisfactory expression levels of the fusion protein, as deemed by an analysis of RNA or protein levels by a person skilled in the art, prior to the initiation of the process described by the invention.

(2) Disruption of the transgenic material is accomplished by any method known to a person skilled in the art, that results in homogenization of the plant tissue and plant cells, in a dry or wetted state. A variety of methods can be chosen from, that suit the source of the plant material. Thus, for seeds, milling is a good way of disrupting the transgenic plant tissue, while for leaves and softer green tissue homogenizing can be accomplished with equipment such as, but not limited to, Waring blender, Sorvall Omnimixer or Polytron homogenizers. Leaves and softer tissue can also be freeze-dried and subsequently milled for homogenization. The equipment for disruption of plant tissue and plant cells is commercially available and easy to scale up as required. General methods of extraction of proteins from plant sources are described by G. Paul Powell in a publication edited by S. Roe, Protein purification applications, 2nd edition (2001). A simple and successful method of extraction of soluble proteins from plant sources is the addition of simple buffers like Low salt buffer to the disrupted, homogenized plant tissue, with thorough mixing. Precautions against oxidative tanning, such as addition of polyvinyl pyrrolidine (1% w/v) are usually sufficient to optimize purification from most plant tissues in order to sequester phenolics from the plant tissue that otherwise could have negative effects on the heterologous protein to be purified. Proteolysis does not always cause problems with plant sources. If, however, proteolysis is a concern, protease inhibitors, such as, e.g., serine-, cysteine- and metalloprotease inhibitors can be added to the extraction buffer. The disruption of the plant material can be done in the presence or absence of a buffered solution. The extraction solution may or may not contain reducing agents such as, but not limited to 2-mercaptoethanol or dithiothreitol (DTT). Soluble plant proteins will be present in the liquid phase together with the CBM-fusion proteins (3) Mixing of liquid with plant material is essential to extract the water-soluble fusion protein to the liquid phase. The liquid added may or may not contain buffering agents to control pH, preferably within the range of about 5.2 to 8.3, it may or may not contain any reducing agents or sequestering agents as described in (2) accordingly to the protein of interest. In its simplest form, the liquid can be water. After thorough mixing of liquid with the disrupted and homogenized plant material, the liquid phase now contains the CBM-fusion protein.

(4) (A) Depending to some degree on the level of homogenization the mixture of disrupted plant material and extraction liquid can be applied directly to an Expanded Bed Adsorption (EBA) column. In this approach the mixture is applied to the column as a stream of fluid through an expanded bed of affinity adsorption matrix of polysaccharide nature. During the streaming through the column the fusion protein in the liquid phase is exposed to the polysaccharide matrix and is selectively adsorbed through the selective affinity of the CBM to the polysaccharide adsorbent media. Particles such as, but not limited to, cell wall fragments and other solids, together with any soluble plant proteins are flushed through the EBA column in the flow-through liquid.

4(B) Alternatively, a majority of the solids in the mixture can be separated from the liquid prior to the affinity binding step through a variety of methods known to a person skilled in the art, these include, but are not limited to, precipitation, filtration, centrifugation, and sedimentation. As described hereinabove, the solids are discarded and the liquid containing the CBM-fusion protein is subjected to an optional heating step 4(C) or applied directly to the affinity binding step (5).

4(C) Heating of the mixture or liquid prior to affinity step (5) is optional, but may act as an additional purifying step in cases where the CBM-fusion protein as a whole remains soluble at elevated temperatures, while soluble plant proteins may denature and precipitate and endogenous plant proteases may be inactivated through heat. For this purpose, the heating procedure, taking into account the nature of the CBM-fusion protein, may involve heating in the range of 50° C. to 100° C., for a period of time in the range of 2 min to 60 minutes during the process. In these embodiments CBM of thermophilic origin are particularly beneficial.

(5) Affinity binding to matrix. The liquid protein extract containing the plant derived CBM-fusion protein is brought into contact with the polysaccharide matrix towards which the CBM has affinity for. The contact can be effected in various ways, such as, but not limited to, chromatography columns packed with the polysaccharide matrix where the liquid is run through the column in either packed or expanded mode, referring to the density of the polysaccharide matrix, or it can be effected in batch mode where the polysaccharide matrix is mixed together with the liquid in a suitable container, with the subsequent recovery of the matrix and the adsorbed CBM-fusion protein. The polysaccharide matrix can be of cellulosic origin such as, but not limited to, Avicel, or it can be of xylanoic origin, such as insoluble xylan. The binding specificity and thermodynamics of CBM9-2 have been studied in detail in a recent publication by Boraston et. al. (2001). It has however surprisingly been found by the present inventors, in contrast to what is indicated in the prior art, that following the methods of the present invention as described herein, CBM9-2 does not bind to plant cell wall components but becomes readily soluble, while retaining good specific binding to a polysaccharide matrix such as used in the affinity adsorption step herein (5). As described herein above this surprising quality introduces several advantages to downstream processing of plant derived CBM-fusion proteins to the extent that a greatly improved downstream processing method is provided.

(6) Washing of the matrix. The polysaccharide affinity adsorbent with CBM-fusion protein bound to it can be washed with several column volumes (relevant quantitative term if the affinity matrix is placed in a chromatography column) of an aqueous solution (e.g. water) or buffer, such as, but not limited to phosphate buffered saline or Tris-based buffers. To improve the efficiency of the washing step, the composition of the washing buffer may be adjusted by means such as, but not limited to, several column volumes of stepwise changes or a gradient of salt concentration or detergent, used to release weakly but nonspecifically bound contaminating proteins from the matrix.

(7) Release of fusion protein from matrix. By using CBM-s with the desired binding characteristics as described herein, elution of the CBM-fusion protein from the affinity matrix can be effected with the exposure of the CBM-fusion protein to competing saccharides such as, but not limited to glucose, galactose, lactose, maltose, and cellobiose. Any of these or other similar saccharides, or a combination thereof, can be added in a suitable amount, such as in the range of 1 mM to 1 M concentration to an elution buffer such as, e.g., phosphate buffered saline or Tris-based buffers, for the elution step. The saccharide concentration can be e.g. in the range 25 mM to 1 M, such as in the range 50-500 mM. These saccharides are commercially available as low-cost bulk chemicals, further improving the overall economy of the downstream processing according to the invention.

(8) Isolation/purification of fusion protein. Further purification/isolation of the CBM-protease may be advantageous or required be in some instances. Such further isolation can be accomplished with any of the commonly available chromatographic procedures known to a person skilled in the art, such as, but not limited to, ion exchange chromatography or size exclusion chromatography.

(9) Final product. The final product is in this case a CBM-protease in a highly purified form, ready for further formulation and packaging in its final form, if necessary.

(10) Isolation of fusion protein containing proteolytic cleavage site. The process described (1-9) for purification of CBM-protease may be the preferred method of purification for any heterologous protein attached to CBM. Such CBM-fusion proteins may or may not contain a proteolytic cleavage site between CBM and the heterologous protein of interest. In a preferred embodiment of the invention described hereinabove the purification process can be utilized together with CBM-protease to cleave a CBM-fusion protein and effectively separate the heterologous protein of interest from CBM-protease and the cleaved CBM. Further isolation of the CBM-fusion protein containing a proteolytic cleavage site may or may not be required or may be advantageous in some instances, before the proteolytic cleavage step (11). This isolation of the fusion protein may also be useful to change the buffer containing the CBM-fusion protein with a proteolytic cleavage site so as to adjust it to conditions favorable for a proteolytic cleavage reaction of step (11). This isolation can be accomplished with any of the commonly available chromatographic procedures known to a person skilled in the art, such as, but not limited to, ion exchange chromatography or size exclusion chromatography.

(11) Proteolytic separation of CBM from heterologous protein fusion partner. At this stage in the process, the CBM-fusion protein containing a proteolytic cleavage site is exposed to a specific protease, fused to CBM but without the cleavage site, which protease is able to recognize the cleavage site and separate the CBM from the heterologous protein of interest. The specific protease linked to CBM is preferably selected from the group of cleavage site-specific proteases, such as enterokinase, Factor Xa, thrombin and the like. After completion of the cleavage reaction, the reaction solution includes released CBM, residual uncleaved CBM-fusion protein, CBM-protease (e.g., CBM-EK), and the released heterologous protein of interest.

(12) Affinity binding of CBM-protease and free CBM to matrix. The solution containing all these components is brought into contact with the polysaccharide matrix which the CBM has affinity for, as described hereinabove in step (5). All CBM-containing components will be adsorbed to the affinity matrix while the released highly purified heterologous protein of interest is recovered in the flow through.

(13) Further isolation of heterologous protein. Although the heterologous protein of interest is already highly purified, further purification/isolation may be required or be advantageous in some instances. This further isolation can be a chromatography step, such as, e.g., ion exchange chromatography or size exclusion chromatography.

(14) Final product. The final product is in this case a heterologous protein in a highly purified form, ready for further formulation (e.g., lyophilization) and packaging in its final form, if necessary.

(15) Washing of the matrix. This step can be performed as described for step (6).

(16) Release of CBM-protease and CBM. Using the elution conditions as described in step (7) above, CBM-protease is brought back in solution. Reconditioning of this solution involves neutralization of conditions and/or removal of the agent(s), (e.g. saccharides) that effected the release of the CBM from the polysaccharide affinity matrix. Said agents can be removed from solution with CBM protease e.g. with ultrafiltration, dialysis, size exclusion chromatography and under certain conditions ion exchange chromatography. Some of these methods such as size exclusion chromatography can in addition purify CBM-protease from residual CBM and CBM-fusion protein, if required.

(17) Recycling of CBM-protease. Once the CBM-protease is reconditioned to a state where it has regained its affinity for said polysaccharide matrix, it can be introduced into the process again for a new round of proteolytic cleavage of CBM-fusion proteins containing proteolytic cleavage site as in step (11). Although the reconstituted CBM-protease solution may contain residual CBM and traces of uncleaved CBM-fusion protein from previous reactions, these will not interfere with the purification of a cleaved heterologous protein fusion partner, as they will co-purify with the CBM-protease. Thus, an efficient recycling of high-value specific CBM-protease improves the efficiency and economy of the novel process of the invention and enables production and purification of recombinantly produced proteins at a large scale, where previously the cost of downstream processing has been prohibitive.

Additional objects, advantages, and novel features of the present invention will become apparent to one ordinarily skilled in the art upon examination of the following examples, which is not intended to be limiting. Additionally, each of the various embodiments and aspects of the present invention as delineated hereinabove and as claimed in the claims section below finds experimental support in the following examples.

EXAMPLES

Example 1

Biomass Interaction Study

CBM9-2 and milled barley seed

Dried barley seed was finely ground in a Retsch mill to a fine flour. 1 g of milled seed was used for the extraction of water-soluble components from the seed with 5 ml of low salt buffer (50 mM potassium phosphate buffer pH 7.02), as a means to rid the sample of all water-soluble components that might interfere with the biomass interaction study. The mixture was vortexed and tumbled for 5 minutes to ensure thorough mixing of the liquid and the milled barley seed material.

Following this mixing, the samples were centrifuged at 5000×g for 4 minutes to pellet the solids. After centrifugation, the supernatant was discarded. This procedure was repeated 3 times with low salt buffer, with the supernatant discarded after each centrifugation. Then the washing procedure was repeated 3 times with high salt buffer (50 mM potassium phosphate buffer pH 7.02, 1 M NaCl), the supernatant discarded as before. The resulting washed solids representing for the most part plant cell-wall fragments and insoluble starch. The washed solids were equilibrated with 3 times washing with low salt buffer as described above, to obtain same conditions that favor affinity binding of CBM9-2 to cellulosic matrix in affinity chromatography. A representative sample of the solids before biomass interaction study was taken for SDS-PAGE analysis (lane 3). 10 µl of bacterially produced CBM9-2 purified on cellulose (AVICEL™)-affinity column (O.D. @280 nm 0.394), were taken for later SDS-PAGE (lane 2). The purified CBM9-2 had previously been subjected to repeated (4×) dilution and concentration in a ultrafiltration module as a proven method for desorbing any bound glucose from the CBM9-2, so as to regain the cellulose binding affinity characteristic of the protein.

Figure 2:
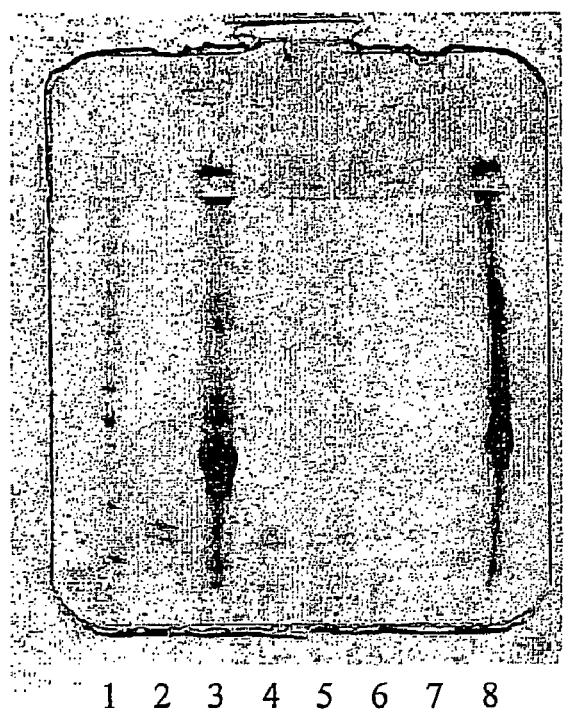
FIG. 2 demonstrates the results obtained from Example 1 by SDS-PAGE analysis. Lane 1: molecular weight size markers, lane 2: purified CBM9-2, lane 3: washed solids from milled barley seed, lane 4: supernatant after biomass interaction, lane 5: first wash with low salt buffer, lane 6: fifth wash with high salt buffer.

2 ml of the purified CBM9-2 were added to the washed, equilibrated solids derived from milled barley seed and the mixture incubated while shaking for 60 minutes at room temperature. After incubation, the mixture was spun down at 5000×g for 10 minutes, and the supernatant subsequently clarified with centrifugation at 13.000×g for 5 minutes. 10 µl of the clarified supernatant from the biomass interaction was taken for SDS-PAGE analysis (lane 4). Subsequently the pellet consisting of the milled barley seed solids, was washed 5 times with low salt buffer and subsequently 5 times with high salt buffer as described above. 10 µl of the first low salt buffer wash (lane 5) and the fifth low salt buffer wash (lane 6), were prepared for subsequent SDS-PAGE analysis. To elute any bound CBM9-2 from the milled barley seed solids, 1 ml of elution buffer (1 M glucose in 50 mM $KPO_4$, pH 7.02) was added to the solids and incubated during mixing for 15 minutes, before centrifugation at 5000×g for 5 minutes and removal of the supernatant (eluate). A 10 µl sample of the eluate was prepared for SDS-PAGE analysis (lane 7). A representative sample from the solids after the biomass interaction study and elution was taken for SDS-PAGE analysis (lane 8). The samples from the biomass interaction assay prepared for SDS-PAGE were run on 12.5% SDS-PAGE gels (PhastGels homogenous 12.5) using PhastSystem (Amersham Pharmacia Biotech). After completion of the run the gel was stained with Coomassie Blue R-250, and destained. The results are illustrated in FIG. 2.

These results demonstrate that CBM9-2 does not bind significantly to plant derived cell-wall fragments or other insoluble solids from milled barley seed.

Example 2

Purification of CBM9-2 from Milled Barley Seed Extract

Barley seeds were milled to finely ground flour using commercially available mill (Aarslev Maskinfabrik, Erhvervsvangen 11, 5792 Aarslev, DK). The resulting barley flour was wetted in Low salt buffer (50 mM potassium phosphate buffer pH 7.02) in volume-ratios 2:3, barley flour:buffer, respectively, The liquid was mixed thoroughly with the flour in a vessel and allowed to sediment overnight at 4° C. CBM9-2 purified from bacteria was added to the barley seed-supernatant.

Figure 3:
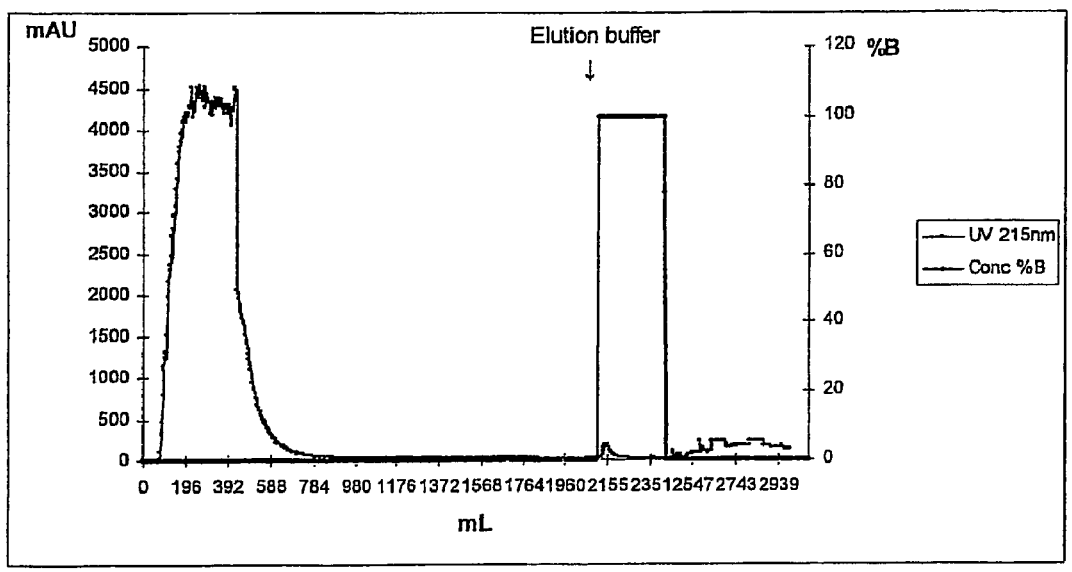
FIG. 3 demonstrates the successful purification of CBM9-2 from milled barley seed extract according to the method of this invention, as described in detail in Example 2. The figure shows the elution profile of an expanded bed absorption (EBA) column with 200 mL cellulose.

The next day the spiked supernatant (100 ml) containing CBM9-2 was fed to to a Streamline 25 (Amersham Biotech) chromatography column containing cellulose (AVICEL™). The feed application was done at flowrate 184 cm/h, in expanded bed mode, followed by a washing step with 5 column volumes high salt buffer (1 M NaCl in 50 mM $KPO_4$, pH 7.02), followed by 5 column volumes of low salt buffer (50 mM $KPO_4$, pH 7.02). The expanded column bed was allowed to sediment (sedimented bed height=20 cm) and elution was performed at 92 cm/h with 300 ml of elution buffer: 1 M glucose in 50 mM $KPO_4$, pH 7.02). The elution conditions resulted in a small peak containing the CBM9-2 protein (see FIG. 3).

This showed that using the procedure described hereinabove that firstly; CBM9-2 remains in solution unattached to cell-wall fragments and other poorly defined solids from milled barley seed, secondly; it is possible to use polysaccharidic affinity chromatography as described by this invention to capture CBM 9-2 from milled barley-seed extract, thirdly; this can be done by using well defined pharmaceutical grade cellulose (AVICEL™) as a matrix, and fourthly; the affinity chromatography step can be done in expanded bed mode as described by the invention, fifthly; the CBM9-2 purified from barley seed-extract can be eluted of the matrix under gentle conditions avoiding any denaturing steps, as described by this invention. The very same conditions and procedure as described hereinabove, can be applied to purify CBM9-2-fusion proteins from transgenic milled seed. Suitable methods of that kind are described by applicant's copending application "A Non-denaturing process to purify recombinant proteins from plants" filed simultaneously with this application and incorporated herein in full by reference.

The polysaccharidic affinity chromatography described is also valid for the separation of protease-CBM and excised CBM from the protein of interest after a proteolytic cleavage reaction, as described by this invention.

Example 3

Purification of Heteroloaous Protein Attached to CBM9-2 from Milled Single Barley Seed Extract In a down-scaled version of the purification procedure described hereinabove, single seeds of transgenic barley plants expressing heterologous protein of interest attached to CBM9-2 were individually homogenized to fine flour. The resulting seed flour was wetted in Low salt extraction buffer (50 mM potassium phosphate buffer pH 7.02, 0.01% polyvinyl pyrrolidine) in volume-ratios 1:7, barley flour:buffer, respectively. The liquid was mixed thoroughly with the single seed flour and the water soluble proteins extracted for 1 hr, with shaking at 5 minute intervals, into the liquid phase at room temperature.

The extract mixture was spun down in a centrifuge at 6000 rpm for 10 minutes. The supernatant (extract) from individual seeds was collected and applied onto a microwell filterplate (MSHVN45, MILLIPORE™) packed with cellulose (AVICEL™). The extracts were added to the cellulose in respective wells with mixing every 3 minutes for 15 minutes at room temperature. After 15 minutes vacuum is applied to microwell plate with the aid of a vacuum manifold (Multi-screen resist vacuum manifold—MAVM0960R, MILLIPORE™) in order to drain the liquid from the cellulose (flow through) in each well. The cellulose is exposed to washing steps, as described in the method described hereinabove: 5 column (i.e. cellulose filled wells) volumes high salt buffer (1 M NaCl in 50 mM $KPO_4$, pH 7.02), followed by 5 column volumes of low salt buffer (50 mM KPO4, pH 7.02). Elution was performed with 250 µl of elution buffer (1 M glucose in 50 mM $KPO_4$, pH 7.02). The eluate was collected by applying vacuum onto the wells of a fresh microwell plate. The eluate was subjected to a highly specific ELISA CBM9-2 analysis, that is based on specific polyclonal antibodies raised against CBM9-2.

The ELISA was performed as follows; 50 µl of appropriately diluted antigen solution (0.1-5 ng protein) were applied to each well of Nunc-Immuno 96MicroWell plates (Cat. no. 442404). Wells were covered with Scotch tape and incubated for 1 hour at 37° C. Antigen solution was shaken out of the wells and the wells washed 3× with 100 µl TBS. Wells were blocked with 100 µl blocking solution per well, covered wells with Scotch tape and incubated for 1 hour at 37° C. After discanting the blocking solution, wells were washed 5× with 100 µl TBS containing 0.01% Tween. Primary antibody raised against CBM9-2 was added appropriately diluted (e.g. 1/3000) in 1% BSA in TBS (50 µl per well) and wells covered with Scotch tape and incubated further at 37° C. for 1 hour. The antibody solution was discanted and the wells washed 10× with TBS containing 0.01% Tween.Secondary antibody (with horseradish peroxidase conjugated) was diluted 1/3000 in 1% BSA in TBS (50 µl per well). Wells covered with Scotch tape and incubated for 1 hour at 37° C. After discanting the solution and washing 8× with 100 µl TBS containing 0.01% Tween and 2× with TBS without Tween, 100 µl of TMB One Solution (Promega™) were added per well and the microplate incubated at room temperature for 30 sek-5 min. When blue color had developed, 100 µl of 0.2 M Sulfuric acid was added. The color turned yellow, and the absorbance was measured in a microplate reader at 450 nm.

Figure 4:
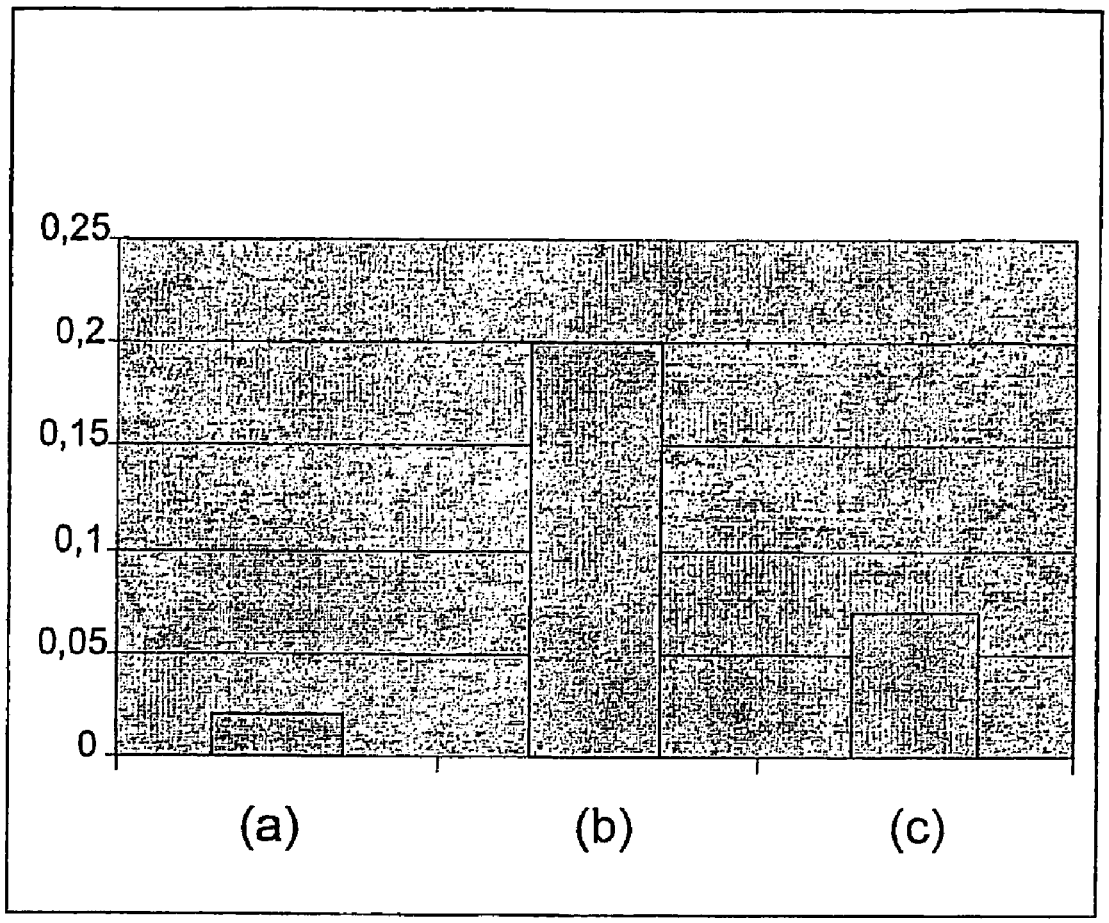
FIG. 4 demonstrates results obtained from Example 3. The graph shows ELSA readings of a control sample and a minimal reading of sample containing a heterologous protein of interest fused to CBM9-2 and purified according to the downscaled version of the purification process described herein. The columns show the measured ELISA values for (a) elution buffer, (b) fusion protein extracted from transgenic seeds, and (c) protein extracted from non-transgenic seeds

Results from an ELISA analysis of a single seed extraction from individual transgenic barley seed are shown in FIG. 4. The ELISA analysis, previously shown to be specific for CBM9-2, shows firstly; that heterologous fusionprotein accumulation in individual seeds can be achieved and verified; that the procedure described hereinabove works for the isolation of a heterologous fusionprotein with cleavage site, even at small scale, supporting the scaleability of the purification process; it shows that the heterologous fusionprotein is not exposed to denaturation during the chromatography process, as it is recognized after elution by the specific antibodies without any renaturation steps being involved, emphasizing the advantage of the present invention to several other harsher affinity chromatography procedures, as discussed hereinabove; that the purification procedure described hereinabove is applicable to any heterologous fusion protein attached to CBM9-2 and not limited to the capture of CBM-protease.

Example 4

Purification and Activity Measurements of CBM-Protease

In order to produce a site-specific protease with a CBM9-2 tag attached to it the following procedure was followed:

*Agrobacterium tumefaciens* strain AGL0 was constructed to contain a binary plasmid carrying an expression construct composed of a constitutive promoter in front of enterokinase cDNA to which was attached cDNA corresponding to CBM9-2, a signal sequence for targeting to Endoplasmic reticulum (ER) and a retention signal to maintain the protein in the ER. This *agrobacterium* strain was grown in YEB media under selection conditions, first in 10 ml for 2 days at 28° C. up to O.D. 600 of 0.8. The small culture is diluted 1:50 to 500 ml culture containing 20 µM acetosyringone for 2-3 days at 28° C. and vigorous shaking up to O.D. 600 nm of 2.5. The bacteria was spun down at 6.000 rpm for 10 minutes and resuspended in MS-solution (containing 55 g/l sucrose) to OD600 2.5. Acetosyringone was added (10 mM), for final concentration of 200 uM. Bacterial suspension was then kept at room temperature for 1 hour and Tween-20 (10%) added, for final concentration of 0.005%.

For transient expression of CBM-protease in lettuce plants were submerged into a bowl containing the *Agrobacterium* bacterial suspension for 15 seconds. Subsequently the plants were placed in a vacuum chamber and 0.4 bar pressure was applied for 20 minutes, after which air inlet was opened to equalize pressure rapidly. The excess bacteria on leaf surface was washed off with successive dipping into bowls of tap water. The lettuce plants were placed in a growth chamber with 16 hrs day/8 hrs night light period at 22° C., for 4 days.

The plants were harvested by excising the leafy tissue and subsequently frozen and kept at 86° C. The plants were homogenized using mortar and liquid nitrogen until a very fine powder was obtained. The powdered lettuce leaf material was extracted by the addition of 1.2:1 (vol:vol) low-salt extraction buffer and lettuce powder respectively, and proteins extracted for 30 minutes with occasional mixing at room temperature.

The extract was subsequently centrifuged at 6000 rpm for 20 minutes to separate solid material and cell wall fragments from liquid phase. The supernatant was decanted and spun again as previously described. The clear supernatant was fed onto a packed bed column containing cellulosic matrix (Avicel™) as described hereinabove. The CBM-protease attached specifically to the cellulosic matrix and after washing the column with 5 column volumes of high salt and low salt washing buffers, respectively, the CBM-protease was eluted off the column under mild, non-denaturing conditions, i.e. with 1 M glucose solution in a single peak.

The peak was subsequently concentrated using Millipore concentrators (Ultrafree-15-Biomax-5).

Enterokinase activity is assayed using specific synthetic substrate according to a standard approach (Grant & Hermon-Taylor, 1979): Synthetic substrate: Gly-Asp-Asp-Asp-Asp-Lys-β-naphthylamide ($GD_4K$-na); Assay conditions 37° C. Reaction volume is 1.5 ml. The reaction mixture consists of: 25 µl 10 mM $GD_4K$-na (0.5 mM), 125 µl 100 mM Tris-HCl, pH 8.4 (25 mM), 50 µl 100% DMSO (10%), 50 µl 100 mM $CaCl_2$ (10 mM), (20-100) µl enterokinase, 250 µl distilled $H_2O$-(20-100) µl. The rate of β-naphthylamine formation was determined from the increment of fluorescence between $\lambda_{ex}$=337 nm and $\lambda_{em}$=420 nm. This was monitored continuously for 5 min.

The results from the activity measurements showed that CBM-enterokinase produced and purified as described, was active; Enterokinase activity was measured to be 442.7 cps/min/µg compared to blank 0.0001 cps/min/µg.

The example shows firstly; that a CMB-protease can be produced in plants, in this case transiently in lettuce, and that CBM-protease can be isolated and purified successfully using the purification procedure described hereinabove. It further shows that the CBM9-2 affinity tag of the fusion protein is fully functional; that the CBM-protease effectively to cellulosic matrix and it can be eluted off the matrix under the mild elution conditions described by the invention, and the eluted protease is shown to be fully active. The enzymatically active purified product provides in itself evidence for the non-denaturing properties of the purification process, as enzyme activity is particularly sensitive for partial or full denaturation, which easily results in loss of activity. This shows effectively that all components of the invention are functional and that their behavior and performance is such that they can easily be applied in the manner described by the invention hereinabove, resulting in a process constituting a major improvement in specificity, economy and efficiency of downstream processing of heterologous proteins of any source.

REFERENCES

Altschul et al., *J. Mol. Biol.* (1990) 215:403-10.

Boraston et al. (2001) Biochemistry 40, pp. 6240-6247.

Contributors (2001) in "Recombinant Protein Drugs" Ed. P. Buckel—from series-Milestones in Drug Therapy, Birkhauser Verlag, Basel 2001.

Grant D. A., Hermon-Taylor J., Biochim. Biophys. Acta 567 (1979), 207-15.

Hammond (1999) in "Plant bioechnology; new products and applications" Eds.

Hammond, McGarvey & Yusibov, Springer Verlag, N.Y. 1999.

IEX, Principles and Methods Series, nr.18-1114-21 —Amersham Pharmacia Biotech.

Kalyanpur M. (2000) in "Downstream processing of proteins" Ed. M. A. Desai Humana Press N.J.

Paul G. Paul Powell G. In Protein purification applications", Ed. by S. Roe, "2nd edition (2001).

R. K. Scopes R. K. (1993) in "Protein Purification: Principles and Practice" 3rd ed. Springer-Verlag NY.

Shani et al. U.S. Pat. No. 6,331,416.

Winterhalter et. al. (1995) Mol. Microbiol. 15 (3), 431-444.

The invention claimed is:

1. A non-denaturing process for obtaining a heterologous protein of interest produced in a plant, comprising
    (a) providing a fusion protein comprising said heterologous protein fused to a carbohydrate binding module (CBM) intercepted by a proteolytic cleavage site, wherein the carbohydrate binding module does not bind to plant cell-wall material and wherein the fusion protein is soluble in a liquid phase obtained from adding extraction liquid to a disrupted plant material,
    (b) contacting said fusion protein with a functional protease fused to a CBM, at conditions facilitating proteolytic cleavage by said protease, to cleave the CBM from the heterologous protein of interest,
    (c) contacting the solution of CBM-protease, free CBM and heterologous protein of interest to a polysaccharide matrix, under conditions where the CBM-protease and free CBM binds to said polysaccharide matrix and where the heterologous protein of interest is not retained on said polysaccharide matrix,
    (d) separating the non-bound heterologous protein of interest from the polysaccharide matrix,
    (e) washing the polysaccharide matrix with the bound CBM-protease and CBM, with one or more suitable aqueous solutions,
    (f) eluting the CBM-protease from the matrix by adjusting conditions effecting the release of said CBM-protease off the matrix; and
    (g) optionally reconditioning said eluted CBM-protease, to retain its affinity to said polysaccharide matrix, such that the reconditioned CBM-protease can be re-used for subsequent repetition of the process defined by steps (a)-(g),
wherein said CBMs are capable of binding reversibly to a polysaccharide matrix and being released from such matrix by non-denaturing elution conditions.

2. The process of claim 1, wherein said protease fused to CBM is from the group of proteases consisting of enterokinase, tobacco etch virus (TEV) protease, factor X and thrombin.

3. The process of claim 2 wherein said protease is mammalian enterokinase (EK) or an enterokinase active part thereof.

4. The process of claim 3, wherein said EK comprises a bovine EK catalytic domain (EKc).

5. The process of claim 4, wherein said bovine EKc is encoded by the nucleic acid sequence shown as SEQ ID NO: 2.

6. The process of claim 1, wherein said protease fused to CBM and said heterologous protein fused to a CBM intercepted by a proteolytic cleavage site are obtained separately by a method for production and purification of a soluble heterologous fusion protein comprising a cellulose binding module (CBM), from transgenic plants or transgenic plant cells expressing said fusion protein, comprising the steps of:
  (a) disrupting the transgenic plant material;
  (b) adding an extraction liquid to the plant material, thereby creating a mixture of soluble and insoluble plant material, so as to extract the soluble fusion protein from said disrupted plant material to the liquid phase to obtain a protein extract; (c) separating the insoluble plant material,
  (c) comprising cell-wall material and solids, from said protein extract comprising said fusion protein of interest;
  (d) contacting said protein extract to a polysaccharide matrix which binds to said fusion protein;
  (e) washing the matrix with the bound fusion protein with one or more suitable aqueous solutions; and
  (f) eluting the fusion protein from said polysaccharide matrix by adjusting conditions effecting the release of said fusion protein from the matrix, thereby obtaining the soluble heterologous fusion protein.

7. The process of claim 6, wherein the separation step (c) comprises a method selected from expanded bed adsorption (EBA), packed mode chromatography, precipitation, filtration, centrifugation, or any combination thereof.

8. The process of claim 6 wherein affinity binding to said polysaccharide matrix in step (d) comprises a chromatography step.

9. The process of claim 6 wherein step (c) and (d) are performed simultaneously in a combined single step.

10. The method of claim 6, combining steps (c) and (d) in a process step comprising expanded bed adsorption with a polysaccharide matrix, as a measure for simultaneous separation of cell-wall material and solids from said protein extract and affinity binding of said CBM-fusion protein onto the polysaccharide matrix.

11. The process of claim 1, wherein said polysaccharide matrix comprises cellulose.

12. The process of claim 11, wherein said cellulose is a pharmaceutically compatible cellulose.

13. The process of claim 12, wherein said cellulose is AVICEL™.

14. The process of claim 1, wherein said reconditioning of the eluted CBM-protease involves neutralization, and/or removal from the CBM-protease eluent of agents that affect the release of CBM from said polysaccharide matrix.

15. The method of claim 14, wherein said reconditioning comprises neutralization or removal from the eluent of carbohydrates such as saccharides.

16. The method of claim 1 wherein said fusion protein comprising said heterologous protein of interest is expressed and retrieved from a transgenic plant or plant cell or by transient expression in a plant, plant tissue or a plant cell.

17. The method of claim 16 wherein said transgenic plant or plant cell is selected from the group of dicotyledonous plants and monocotyledonous plants.

18. The method of claim 17 wherein said plant cell or transgenic plant is selected from the group of plants including tobacco, rapeseed, soy bean, alfalfa, lettuce, barley, maize, wheat, oat and rice.

19. The method of claim 1, wherein said CBM fused to said heterologous protein and said CBM fused to said protease are heat-stable and remain soluble at elevated temperatures.

20. The method of claim 19, wherein one or both of said CBMs are a CBM encoded by a region of the xylanase 10A gene from *Thermotoga maritima*.

21. The method of claim 20, wherein one or both of said CBMs are encoded by a sequence comprising the sequence shown as SEQ ID NO: 1, or a sequence encoding the same amino acid sequence or an amino acid sequence with at least 80% sequence identity to said sequence.

* * * * *